(12) United States Patent
Kennington et al.

(10) Patent No.: US 12,402,834 B1
(45) Date of Patent: Sep. 2, 2025

(54) WRIST-MOUNTED MONITORING SYSTEM

(71) Applicants: Jason Kennington, Street, MD (US); Drew Harlacher, Delta, PA (US); Cyrus Robert Etemad-Moghadam, Fallston, MD (US); Brian Ghezzi, Forest Hill, MD (US); Laura Zawadowicz, Forest Hill, MD (US)

(72) Inventors: Jason Kennington, Street, MD (US); Drew Harlacher, Delta, PA (US); Cyrus Robert Etemad-Moghadam, Fallston, MD (US); Brian Ghezzi, Forest Hill, MD (US); Laura Zawadowicz, Forest Hill, MD (US)

(73) Assignee: Hindsight Systems, LLC, Jarrettsville, MD (US)

( * ) Notice: Subject to any disclaimer, the term of this patent is extended or adjusted under 35 U.S.C. 154(b) by 590 days.

(21) Appl. No.: 17/892,059

(22) Filed: Aug. 20, 2022

Related U.S. Application Data

(60) Provisional application No. 63/235,249, filed on Aug. 20, 2021.

(51) Int. Cl.
*A61B 5/00* (2006.01)
(52) U.S. Cl.
CPC .................... *A61B 5/681* (2013.01)
(58) Field of Classification Search
CPC ...................................... A61B 5/681
USPC ...................................... 340/573.4
See application file for complete search history.

(56) References Cited

U.S. PATENT DOCUMENTS

| | | | |
|---|---|---|---|
| 5,612,675 A | | 3/1997 | Jennings et al. |
| 5,627,520 A | * | 5/1997 | Grubbs ..................... G07C 9/28 455/100 |
| 5,883,576 A | * | 3/1999 | De La Huerga ......... G07C 9/28 340/8.1 |
| 5,969,613 A | * | 10/1999 | Yeager ................ E05B 73/0017 340/568.1 |
| 6,092,401 A | | 7/2000 | Sankey et al. |
| 6,311,531 B1 | | 11/2001 | Sykes |

(Continued)

FOREIGN PATENT DOCUMENTS

| | | |
|---|---|---|
| EP | 3382664 | 10/2018 |
| WO | WO174474 | 9/2020 |

OTHER PUBLICATIONS

Seccino Technologies Co., Ltd, "Tamper Proof GPS Tracker Ankle Tracking Bracelet for House Arrest Offender Parolee Bail Out:" Printed Feb. 15, 2021. 9 pages.

*Primary Examiner* — Omar Casillashernandez
(74) *Attorney, Agent, or Firm* — Joseph E. Maenner; Maenner & Associates, LLC

(57) ABSTRACT

A monitoring system includes a strap having a free end and a base end, a base attached to the base end of the strap, and at least one contact pad attached to the base. An electrical conductor extends along the strap between the free end and the base end. An electronic module is releasably attached to the base and includes a processor, a power supply, a transmitter, and a locking pin. A locking mechanism is configured to retain the electronic module on the base and includes a biasing member mounted on the base, a locking pawl operable between a locking position and a release position. The free end of the strap is releasably insertable between the module and the base. A key is insertable into the base and configured to release the locking pawl from the locking pin.

20 Claims, 7 Drawing Sheets

(56) References Cited

U.S. PATENT DOCUMENTS

| | | | |
|---|---|---|---|
| 6,385,134 B1* | 5/2002 | Lange | G01L 19/16 |
| | | | 73/299 |
| 6,922,148 B2 | 7/2005 | Despotis | |
| 7,864,059 B2* | 1/2011 | Lee | G08B 21/0202 |
| | | | 368/327 |
| 2010/0224443 A1* | 9/2010 | Broten | A63B 29/08 |
| | | | 74/577 M |
| 2020/0250953 A1* | 8/2020 | Wojcik | G08B 21/22 |

* cited by examiner

WRIST-MOUNTED MONITORING SYSTEM

CROSS-REFERENCE TO RELATED APPLICATION

The present application claims the benefit of U.S. Provisional Patent application Ser. No. 63/235,249, filed on Aug. 20, 2021, which is incorporated herein by reference in its entirety.

BACKGROUND OF THE INVENTION

Field of the Invention

The invention relates to electronic personal monitoring systems that are worn by a user.

Description of the Related Art

Occasionally, when a person is under arrest that person is released to "house arrest" to allow the person to live outside of the prison, but with restrictions regarding their movement ability. The person is typically required to wear some type of monitoring system that monitors the location of the person and informs authorities if the person leaves their home or other designated location. The monitoring system is typically large and can stigmatize the person when others see the monitoring system and realize that the person wearing the monitoring system is under house arrest.

Also, wearers sometimes try to "escape" the monitoring by removing the monitoring system in such a way as to not alert authorities that the monitoring system has been removed.

It would be beneficial to provide a monitoring system that does not look like a known monitoring system and also is difficult, if not impossible, to remove without alerting authorities that the monitoring system has been removed.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a monitoring system comprising a strap having a free end and a base end, a base attached to the base end of the strap, and at least one contact pad attached to the base. An electrical conductor extends along the strap between the free end and the base end. The electrical conductor is electrically connected to the at least one contact. An electronic module is releasably attached to the base and includes a processor, a power supply electrically connected to the electrical conductor at the base end of the strap, a transmitter, and a locking pin. A locking mechanism is configured to retain the electronic module on the base. The locking mechanism comprises a biasing member mounted on the base and a locking pawl operable between a locking position and a release position. The biasing member biases the locking pawl toward the locking position and engage the locking pin when the electronic module is attached to the base. The free end of the strap is releasably insertable between the module and the base.

The present invention also provides a key that is insertable into the base and configured to release the locking pawl from the locking pin.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
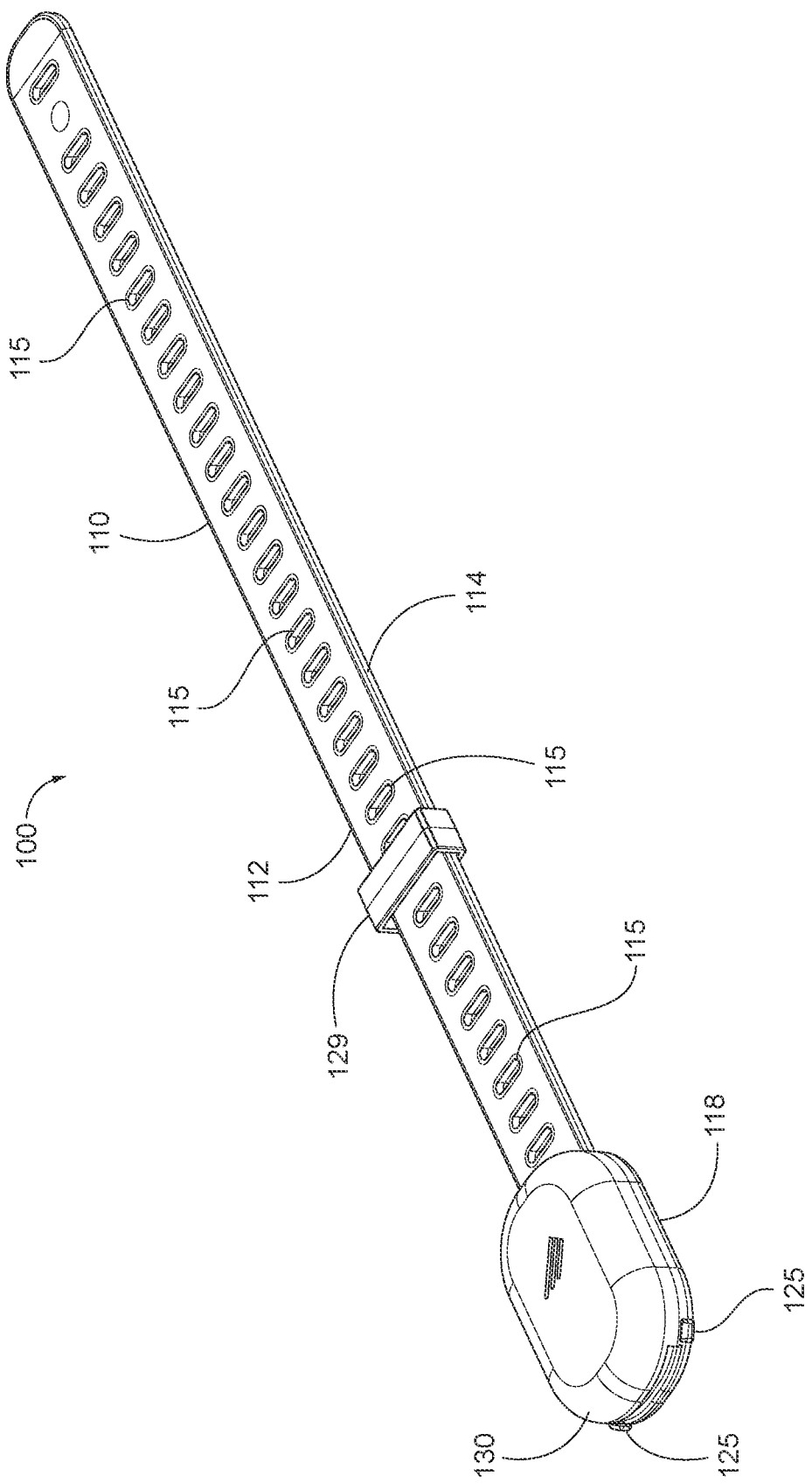
FIG. 1 is perspective view of a wrist-mounted monitoring system according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The wrist-mounted monitoring system according to the present invention is similar to known ankle-mounted monitoring systems that are used to monitor the location and movement of the wearer, such as those under house arrest or are otherwise subject to official monitoring, but does not include the stigma associated with wearing the ankle-mounted monitoring system.

Figure 1A:
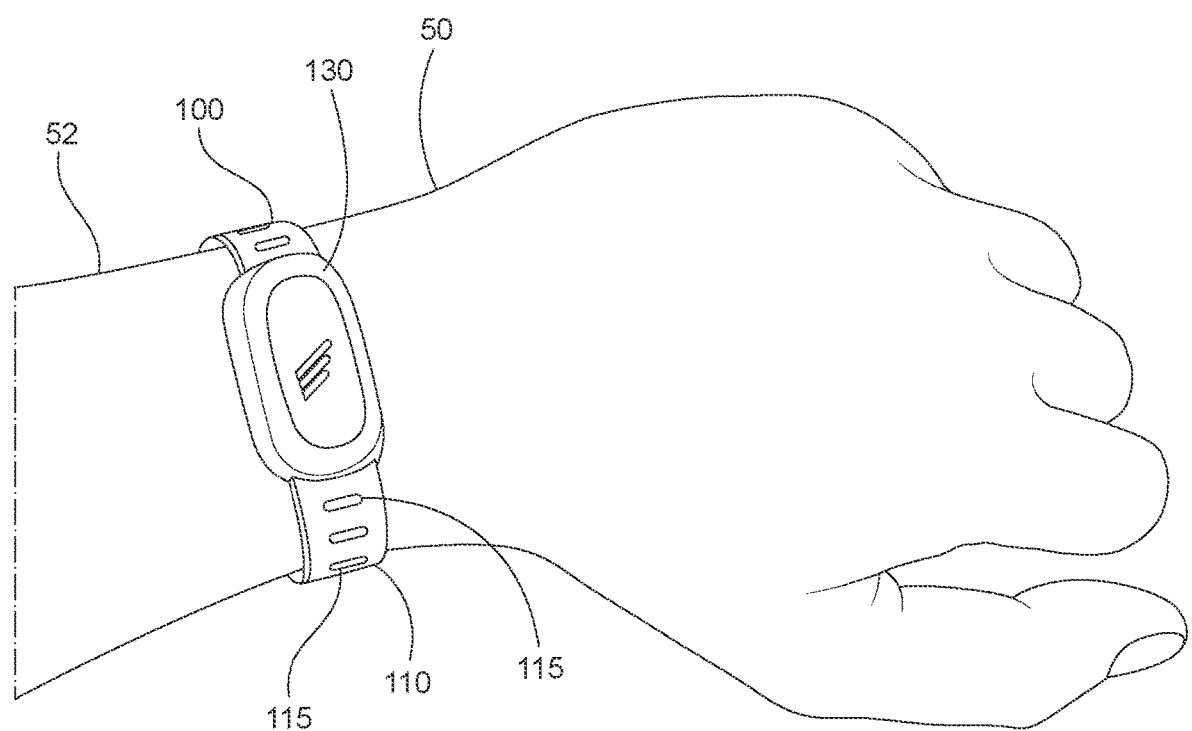
FIG. 1A is a perspective view of the system of FIG. 1 mounted on a wrist.

Referring to the Figures, a wrist-mounted monitoring system 100 according to an exemplary embodiment of the present invention is shown in FIG. 1 and includes a wrist strap 110 and a module 130 that houses operational electronics such as a CPU 139 (shown in FIG. 1B) and a locking/unlocking mechanism 132 in a housing 134. Locking/unlocking mechanism 132 requires the use of a special key 150 to release locking/unlocking mechanism 132 and allow strap 110 to be removed from the wrist 52 of a wearer 50. FIG. 1A shows the system attached to wrist 52 of wearer 50.

Figure 1B:
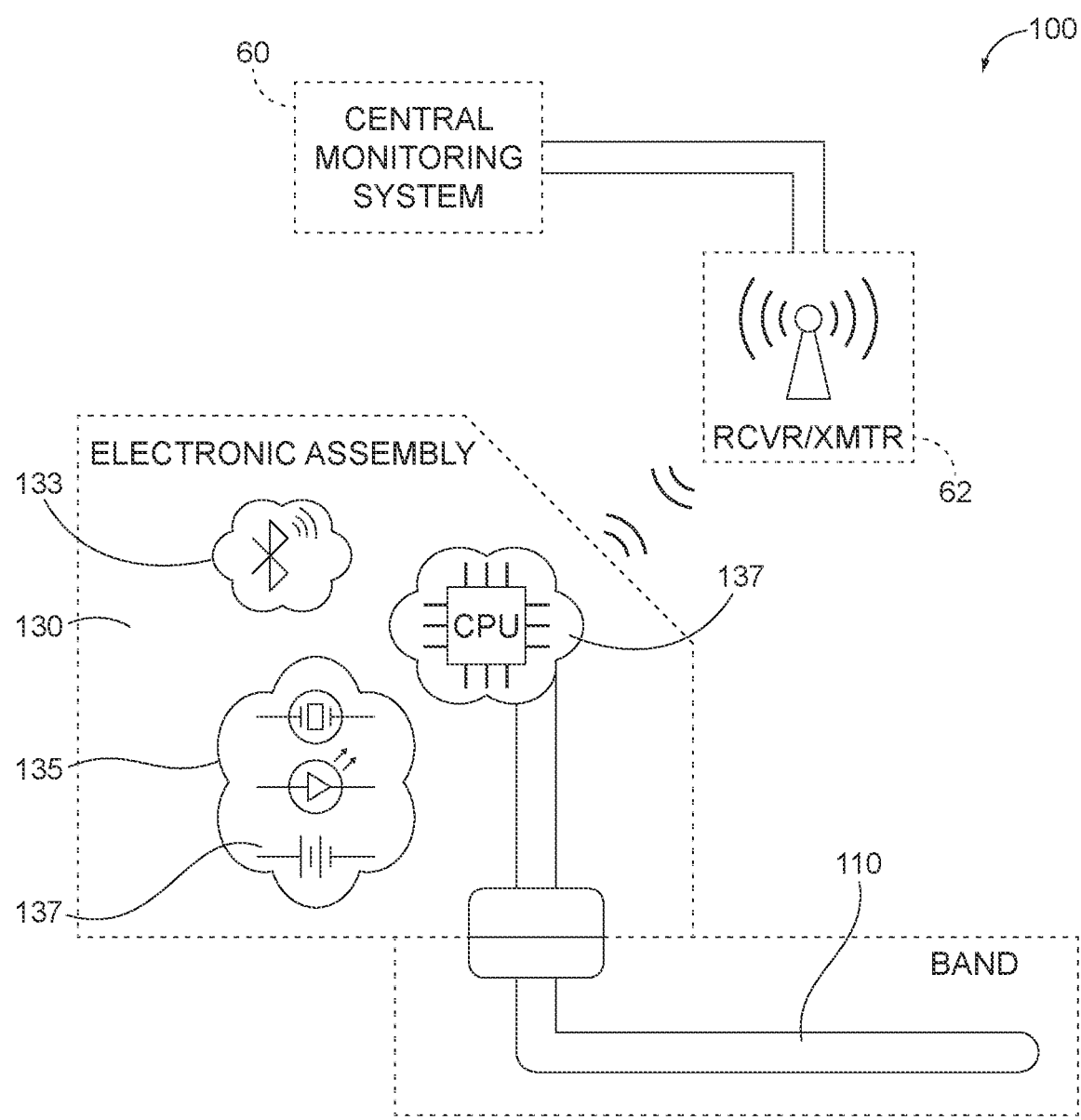
FIG. 1B is a schematic drawing of exemplary electronics used with the system of FIG. 1.
Figure 2:
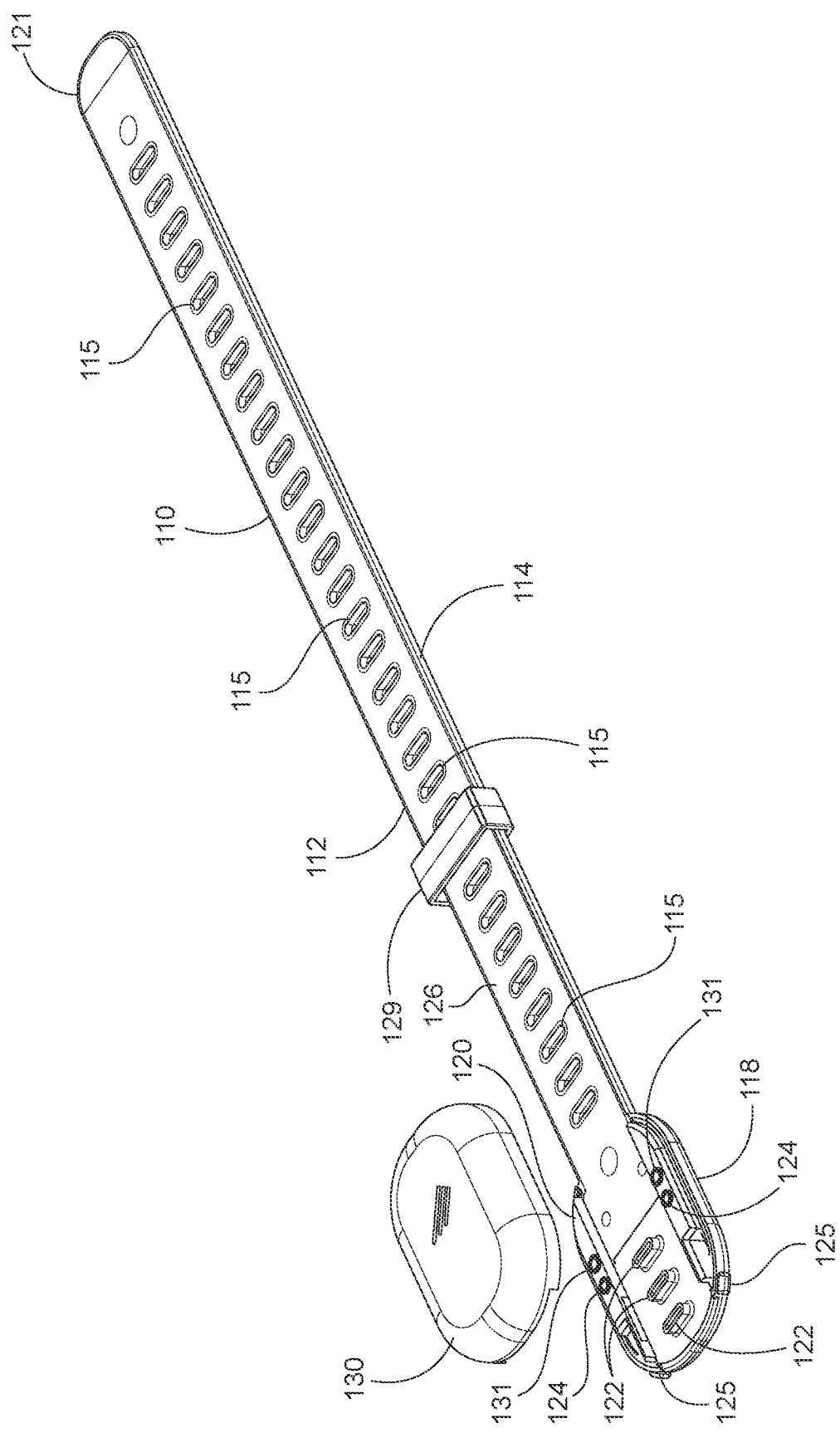
FIG. 2 is an exploded perspective view of the system of FIG. 1.
Figure 3:
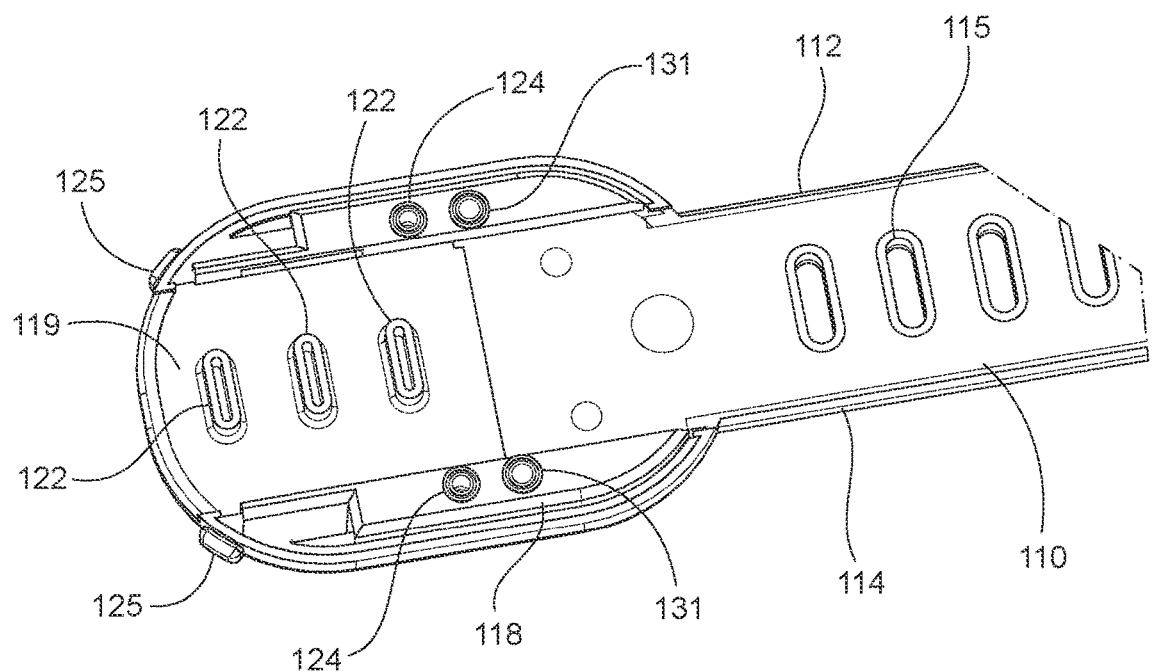
FIG. 3 is an enlarged perspective view of a base end of the system of FIG. 1.

Referring to FIG. 1B, monitoring system 100 wirelessly communicates with a central monitoring system 60 through a receiver/transmitter 62 to monitor the location of monitoring system 100.

Referring to FIGS. 1-4, strap 110 is constructed from a generally planar elongate flexible material such as, for example, a polymer. Strap 110 includes a first edge 112, an opposing second edge 114, and a plurality of transversely extending generally oval through-openings 115 formed between first edge 112 and second edge 114 and evenly spaced along a length of strap 110.

Figure 4:
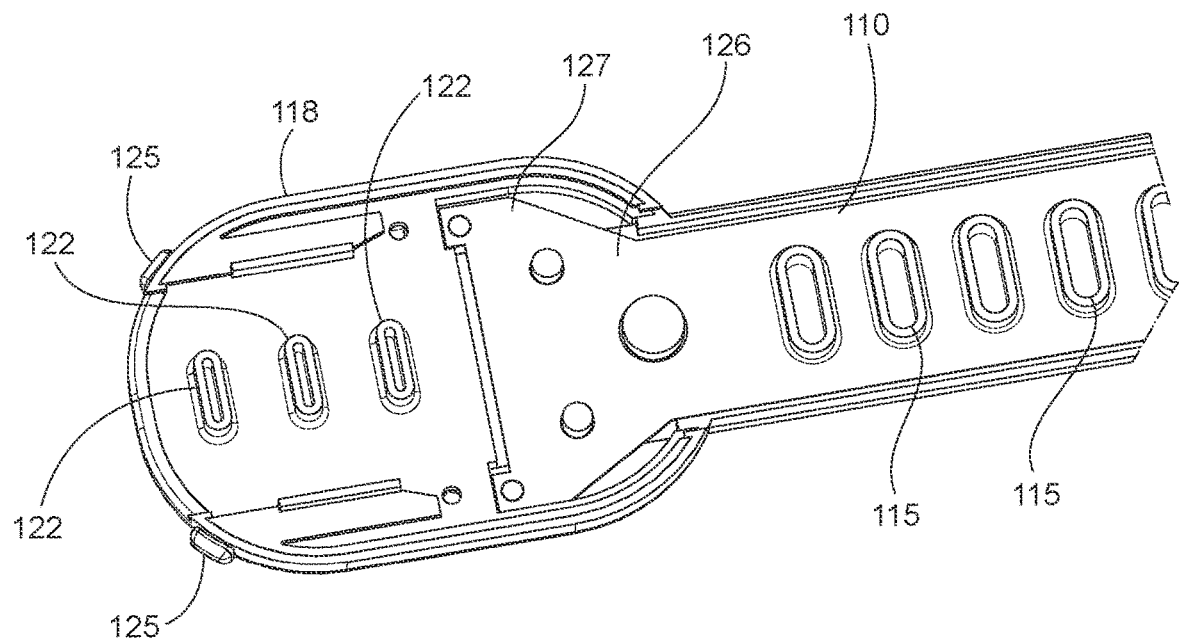
FIG. 4 is an enlarged perspective view of the base end of the system of FIG. 1, showing an electrical conductor in the strap.

A base 118 for module 130 is located at a base end 120 of strap 110 and a free end 121 of strap 110 is located distal from base end 120. Base 118 includes a platform 119 having openings for a plurality of raised oval tabs 122 spaced to allow insertion of tabs 122 into a like plurality of through-openings 115 when strap 110 is wrapped around the wrist 52 of wearer 50 and monitoring system 100 is secured to the wrist 52. Tabs 122 extend upwardly from base 118, as shown in FIG. 4. Base 118 also includes a pair of slots 123 distal from strap 110 that allow key 150 to be inserted therein to remove module 130 from base 118. The entrance to slots 123 can be covered with removable rubber inserts 125 to prevent water an/or dirt from entering into slots 123 and possibly interfering with the operation of key 150 when key 150 is inserted into slots 123.

Strap 110 also includes a conductor 126 extending along a length of strap 110. Conductor 126 is used to complete an electrical circuit when monitoring system 100 is wrapped around wrist 52 of wearer 50 so that, if strap 110 is cut, the electrical circuit is also cut. Conductor 126 has a base end 127 attached to base 118 and electrically connected to contact pads 131 in base 118. Contact pads 131 will provide for an electrical connection to module 130 when module 130 is attached to base 118.

A strap retainer 129 is slidingly mounted on strap 110. Strap retainer 129 is used to retain free end 132 when strap 110 is wrapped around wrist 52. Strap retainer 129 is slidable to accommodate different wrist thicknesses.

Base 118 is a generally planar, oval shaped base constructed from a rigid material, such as polycarbonate/nylon. Base 118 supports and retains module 130. Module 130 houses all electronics, such as CPU 139, wireless transmitter 133 (to transmit location and other information to monitoring system 60), and other electronic components 135, including a battery 137, that are used to operate monitoring system 100, shown in FIG. 1B. Module 130 also houses a locking mechanism 132 that releasably retains module 130 onto base 118.

Figure 5:
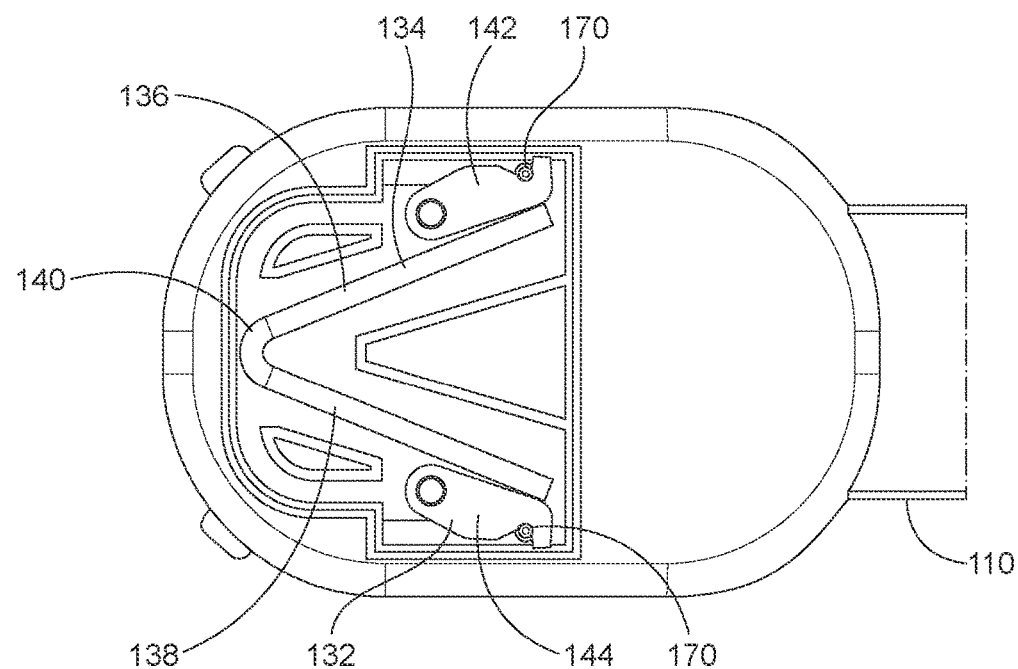
FIG. 5 is a top plan view of the base end of the system of FIG. 1, showing a locking mechanism engaged with a locking pin.
Figure 6:
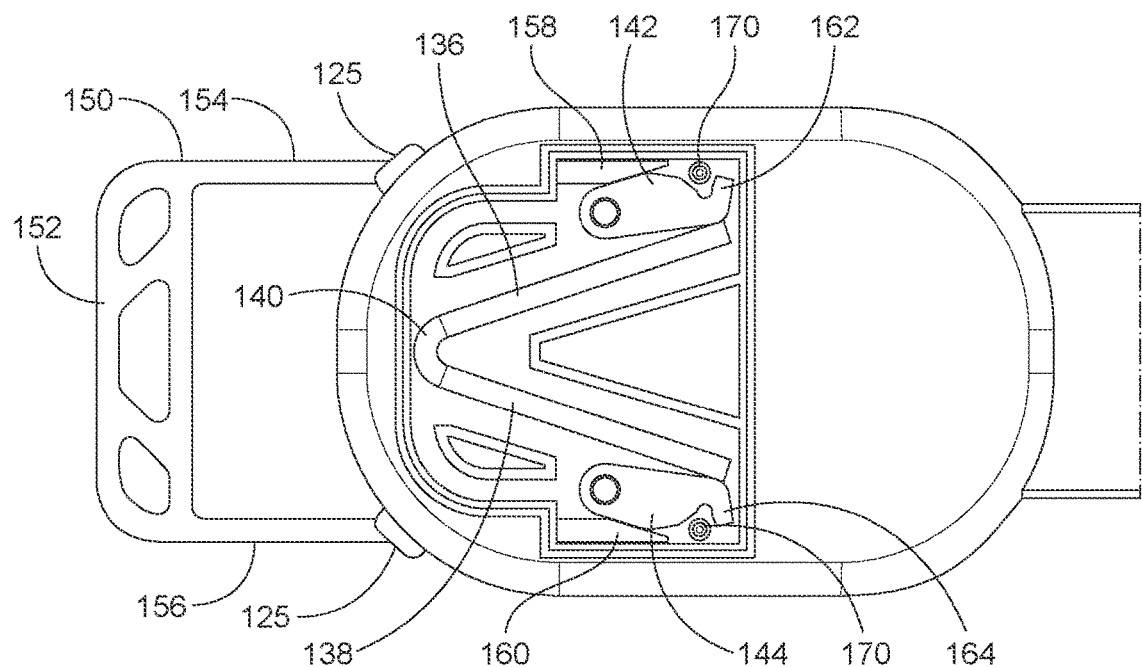
FIG. 6 is a top plan view of the base end of the system of FIG. 5, showing a key inserted into the locking mechanism and the locking mechanism disengaged from the locking pin.

Referring to FIGS. 5 and 6, locking mechanism 132 includes a single biasing member 134 in the form of a torsion spring that is located below platform 119. Biasing member 134 is a single piece torsion spring with a first leg 136 and a second leg 138 connected at an acute angle at an apex 140. First leg 136 and second leg 138 are biased away from each other. Each leg 136, 138 is in contact with a locking pawl 142, 144, respectively, that has a pivot end 146, 148, respectively, and an engaging end 162, 164, respectively.

Figure 7:
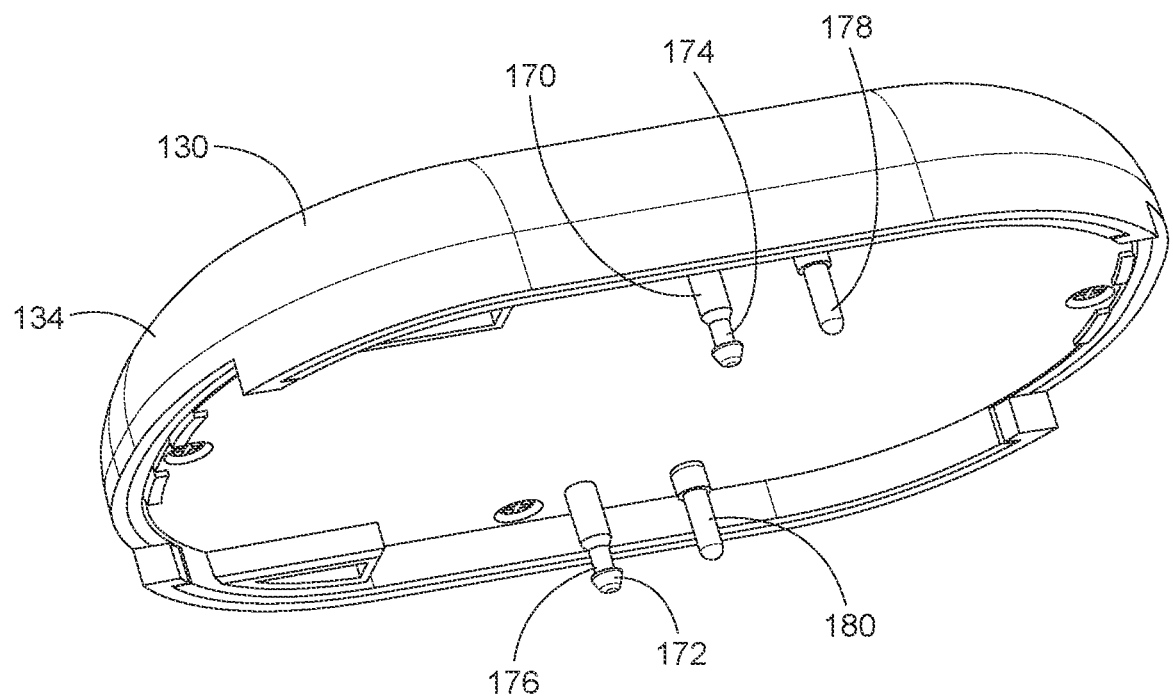
FIG. 7 is a bottom perspective view of a module used with the system of FIG. 1.

Engaging ends 162, 164 are biased by biasing member 134 away from each other and into engagement with locking pins 170, 172, respectively, when module 130 is attached to base 118 (Locking pins 170, 172 are shown in FIG. 7). Each locking pin 170, 172 has a recessed portion 174, 176, that receives an engaging end 162, 164 so that module 130 is secured to base 118, with strap 110 secured in between module 130 and base 132 around wrist 52 so that monitoring system 100 cannot be removed from wrist 52 without using key 150. Locking pins 170, 172 fit into pin holes 124 in base 118 to secure locking pins 170, 172 with base 118.

Referring to FIG. 7, a pair of pogo pins 178, 180 extend from module 130 and are used to engage conductor 126. When module 130 is fixed over base 118, pogo pins 178, 180 engage contact pads 131 in module 130 such that pogo pins 178, 180 electrically connect conductor 126 to CPU 139.

To secure monitoring system 100 around a wrist 52, wrist 52 is held out, palm side down. Base 118 is placed on top of wrist 52 and strap 110 is wrapped around wrist 52. Through openings 115 in strap 110 are aligned with tabs 122 on base 118 to secure strap 110 to base 118. Module 130 is then snapped onto base 118 such that locking pins 170, 172 engage their respective locking pawls 142, 144 to secure module 130 onto base 118.

Contact is made by pogo pins 178, 180 when free end 121 of strap is placed over base 118 and module 130 is snapped onto base 118. An electrical circuit is formed from battery 137, to CPU 139, to base end 127 of conductor 126, to free end 121 of conductor 126, to pogo pins 178, 180, and back to battery 137. When the electrical circuit is complete, transmitter 133 transmits to receiver 62, indicating that system 100 is secured to the wearer 50 and that the location of the system 100 and the wearer 50 are known. When the electrical circuit is broken, either by removing module 130 from base 118, by cutting strap 110, or otherwise, transmission from transmitter 133 to receiver 62 stops and an alarm can be sounded via monitoring system 60 that system 100 is no longer being worn by the wearer 50, and that the location of wearer 50 is now in doubt.

Figure 8:
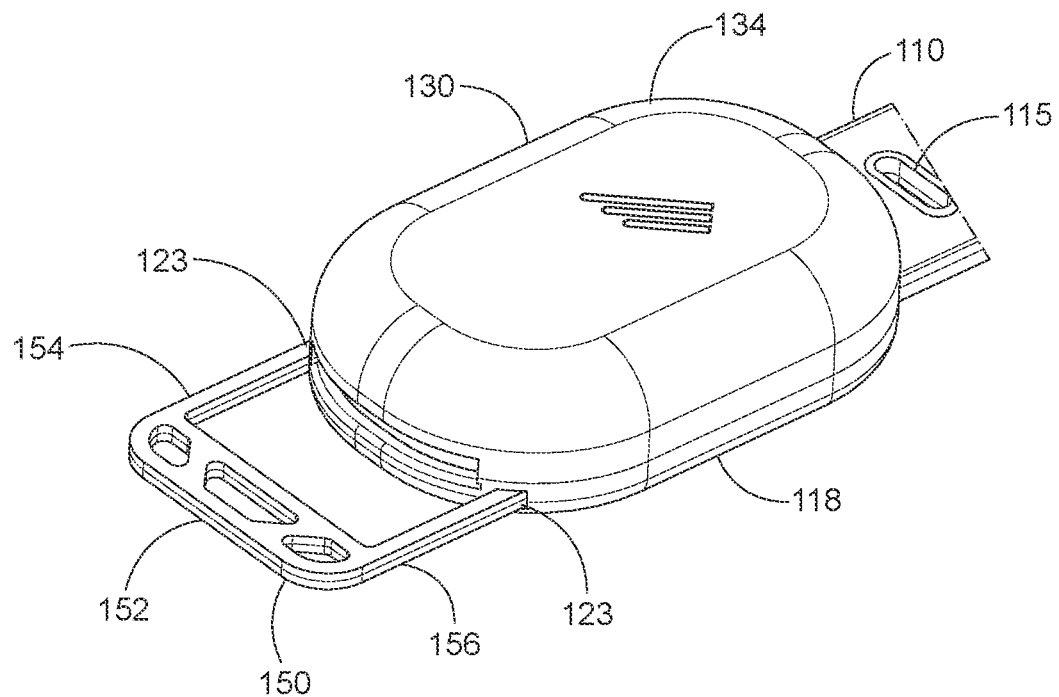
FIG. 8 is a perspective view of the base end with module and the key inserted into the base.

Key 150 is shown in FIGS. 6 and 8. Key 150 is used to release locking mechanism 132 so that strap 110 can be loosened from base 118 and removed from wrist 52. Key 150 is generally U-shaped and includes a handle 152 with two parallel extending legs 154, 156.

Each leg 154, 156 has a tapered tip 158, 160, respectively, with each taper facing the opposing leg 156, 154. To use key 150, legs 154, 156 are inserted into release openings 123 and advanced into base 118 until tips 158, 160 engage pawls 142, 144 and bias engaging ends 162, 164 of pawls 142, 144 toward each other, moving pawls 142, 144 out of engagement with locking pins 170, 172. When pawls 142, 144 are disengaged from locking pins 170, 172, module 130 can be removed from base 118. With module 130 removed from base 118, free end 121 of strap 110 can be removed from base 118 and strap 110 can be removed from wrist 52. Monitoring system 100 is configured such that free end 121 of strap 110 is configured to be removed from base 118 only when electronic module 130 is removed from base 118.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A monitoring system comprising:
a strap having a free end and a base end;
a base attached to the base end of the strap;
at least one contact pad attached to the base;
an electrical conductor extending along the strap between the free end and the base end, wherein the electrical conductor is electrically connected to the at least one contact;
an electronic module releasably attached to the base, the electronic module comprising:
a processor;
a power supply electrically connected to the electrical conductor at the base end of the strap;
a transmitter; and
a locking pin; and
a locking mechanism configured to retain the electronic module on the base, the locking mechanism comprising:
a biasing member mounted on the base;
a locking pawl operable between a locking position and a release position, the biasing member biasing the locking pawl toward the locking position and engaging the locking pin when the electronic module is attached to the base;
wherein the free end of the strap is releasably insertable between the module and the base.

2. The monitoring system according to claim 1, wherein the electronic module further comprises a pogo pin extending therefrom, the pogo pin configured to engage the electrical conductor.

3. The monitoring system according to claim 2, wherein, when the free end of the strap is inserted into the base, an electrical circuit is formed from the power supply to the processor to the electrical conductor at the base end of the strap, through the electrical conductor to the free end of the strap, to the pogo pin, and back to the power supply.

4. The monitoring system according to claim 1, further comprising a key insertable into the base and configured to release the locking pawl from the locking pin.

5. The monitoring system according to claim 4, wherein the key comprises a leg configured to engage the locking pawl and bias the locking pawl away from the locking pin.

6. The monitoring system according to claim 4, wherein the locking pawl is mounted on the base.

7. The monitoring system according to claim 1, wherein the biasing member comprises a torsion spring.

8. The monitoring system according to claim 7, wherein the torsion spring comprises a first leg and a second leg connected to each other at an acute angle at an apex.

9. The monitoring system according to claim 1, wherein the free end of the strap is configured to be removed from the base only when the electronic module is removed from the base.

10. The monitoring system according to claim 1, wherein the strap includes at least one through opening at the free end and wherein the base comprises a tab configured to be inserted into the at least one through opening such that, when the electronic module is attached to the base, the free end of the strap is secured between the electronic module and the base.

11. A monitoring system comprising:
a strap having a free end and a base end;
a base attached to the base end of the strap;
at least one contact pad attached to the base;
an electrical conductor extending along the strap between the free end and the base end, wherein the electrical conductor is electrically connected to the at least one contact;
an electronic module releasably attached to the base, the electronic module comprising:
a processor;
a power supply electrically connected to the electrical conductor at the base end of the strap;
a transmitter;
a pogo pin extending therefrom, the pogo pin configured to engage the electrical conductor; and
a locking pin; and
a locking mechanism configured to retain the electronic module on the base, the locking mechanism comprising:
a biasing member mounted on the base;
a locking pawl mounted on the base and operable between a locking position and a release position, the biasing member biasing the locking pawl toward the locking position and engaging the locking pin when the electronic module is attached to the base;
wherein the free end of the strap is releasably insertable between the module and the base; and a key insertable into the base and configured to release the locking pawl from the locking pin, the key comprising:
a leg configured to engage the locking pawl and bias the locking pawl away from the locking pin.

12. The monitoring system according to claim 11, wherein the system is configured to be worn on a wrist.

13. The monitoring system according to claim 11, further comprising a receiver configured to receive electronic signals from the transmitter.

14. The monitoring system according to claim 13, wherein, when the electronic module is attached to the base, an electrical circuit is formed along the strap and the electronic signals are transmitted from the transmitter to the receiver.

15. The monitoring system according to claim 14, wherein, when the electronic module is not attached to the base, the electrical circuit is broken and the electronic signals are not transmitted from the transmitter to the receiver.

16. The monitoring system according to claim 14, wherein, when the strap is cut, the electrical circuit is broken and electronic signals are not transmitted from the transmitter to the receiver.

17. The monitoring system according to claim 11, wherein the locking pin has a recessed portion configured to receive an engaging end of the locking pawl.

18. The monitoring system according to claim 11, wherein the free end of the strap is configured to be removed from the base only when the electronic module is removed from the base.

19. The monitoring system according to claim 11, wherein the key has a first leg and a second leg configured to be inserted into the base.

20. The monitoring system according to claim 11, wherein, when the free end of the strap is inserted into the base, an electrical circuit is formed from the power supply to the processor to the electrical conductor at the base end of the strap, through the electrical conductor to the free end of the strap, to the pogo pin, and back to the power supply.

* * * * *